(12) United States Patent
Schultz et al.

(10) Patent No.: US 12,016,702 B2
(45) Date of Patent: *Jun. 25, 2024

(54) SINGLE RADIO-TRANSPARENT CONNECTOR FOR MULTI-FUNCTIONAL REFERENCE PATCH

(71) Applicant: BIOSENSE WEBSTER, INC., Irvine, CA (US)

(72) Inventors: Jeffrey W. Schultz, Chino, CA (US); Keshava Datta, Chino Hills, CA (US)

(73) Assignee: Biosense Webster Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/059,401

(22) Filed: Nov. 28, 2022

(65) Prior Publication Data

US 2023/0086931 A1  Mar. 23, 2023

Related U.S. Application Data

(63) Continuation of application No. 15/194,200, filed on Jun. 27, 2016, now Pat. No. 11,510,621, which is a
(Continued)

(51) Int. Cl.
*A61B 5/05* (2021.01)
*A61B 5/00* (2006.01)
(Continued)

(52) U.S. Cl.
CPC ............ *A61B 5/6833* (2013.01); *A61B 5/053* (2013.01); *A61B 5/062* (2013.01); *A61B 5/063* (2013.01);
(Continued)

(58) Field of Classification Search
CPC . A61B 2034/2051; A61B 5/053; A61B 5/062; A61B 5/6833; A61B 34/20;
(Continued)

(56) References Cited

U.S. PATENT DOCUMENTS 3,606,881 A   9/1971   Woodson
3,829,826 A   8/1974   Brown et al.
(Continued)

FOREIGN PATENT DOCUMENTS

CA   2 762 280       6/2012
EP   1 854 405 A1   11/2007
(Continued)

OTHER PUBLICATIONS

Canadian Intellectual Property Office Action dated Oct. 19, 2015 for Application No. 2,728,536, 6 pages.
(Continued)

*Primary Examiner* — Adam Z Minchella
(74) *Attorney, Agent, or Firm* — Frost Brown Todd LLP

(57) ABSTRACT

A patch and sensor assembly has a biosensor housed in a reusable portion that connects to a mapping and localization system (MLS) via biosensor wires. A disposable portion has an electrode layer through which signals are transmitted to the MLS via ACL wires. The biosensor and ACL wires extend through a single cable exiting the reusable portion. The disposable portion includes an adhesive layer for adhering the electrode layer to a patient, on the electrode layer, and an engagement element for detachably receiving at least a portion of the housing of the reusable portion. The reusable portion includes a housing in which the biosensor has biosensor wires that exit the reusable portion. The housing is also adapted to carry and/or provide support to an ACL contact member responsive to the electrode layer of the disposable portion, and ACL wires that exit the reusable portion.

20 Claims, 10 Drawing Sheets

Related U.S. Application Data continuation of application No. 12/977,881, filed on Dec. 23, 2010, now Pat. No. 9,375,179.

(51) Int. Cl.
  *A61B 5/053* (2021.01)
  *A61B 5/06* (2006.01)

(52) U.S. Cl.
  CPC .............. *A61B 2560/0412* (2013.01); *A61B 2562/0215* (2017.08); *A61B 2562/17* (2017.08)

(58) Field of Classification Search
  CPC . A61B 5/274; A61B 5/063; A61B 2562/0215; A61B 2562/17; A61B 2560/0412
  See application file for complete search history.

(56) References Cited

U.S. PATENT DOCUMENTS

| | | |
|---|---|---|
| D240,166 S | 6/1976 | Cartmell et al. |
| 4,112,941 A | 9/1978 | Larimore |
| 4,209,020 A | 6/1980 | Nielsen |
| 4,490,005 A | 12/1984 | Hovey |
| 4,635,642 A | 1/1987 | Cartmell et al. |
| 4,653,503 A | 3/1987 | Heath |
| 4,685,467 A | 8/1987 | Cartmell et al. |
| 4,827,939 A | 5/1989 | Cartmell et al. |
| 4,947,846 A | 8/1990 | Kitagawa et al. |
| 5,199,432 A | 4/1993 | Quedens |
| 5,265,579 A | 11/1993 | Ferrari |
| 5,355,883 A | 10/1994 | Ascher |
| 5,391,199 A | 2/1995 | Ben-Haim |
| 5,443,489 A | 8/1995 | Ben-Haim |
| 5,467,768 A | 11/1995 | Suda et al. |
| 5,499,628 A | 3/1996 | Wright |
| 5,571,165 A | 11/1996 | Ferrari |
| 5,615,674 A | 4/1997 | Maurer |
| 5,782,761 A | 7/1998 | Gusakov |
| 5,879,373 A | 3/1999 | Röper et al. |
| 5,928,142 A | 7/1999 | Cartmell et al. |
| 5,978,693 A | 11/1999 | Hamilton et al. |
| 6,117,077 A | 9/2000 | Del Mar et al. |
| 6,129,668 A | 10/2000 | Haynor et al. |
| 6,324,432 B1 | 11/2001 | Rigaux et al. |
| 6,381,485 B1 | 4/2002 | Hunter et al. |
| 6,546,271 B1 | 4/2003 | Reisfeld |
| 6,650,922 B2 | 11/2003 | Kurata et al. |
| 6,690,963 B2 | 2/2004 | Ben-Haim et al. |
| 6,780,065 B2 | 8/2004 | Schwarz |
| 6,788,967 B2 | 9/2004 | Ben-Haim et al. |
| 6,912,414 B2 | 6/2005 | Tong |
| 7,104,801 B1 | 9/2006 | Brodnick et al. |
| 7,110,804 B2 | 9/2006 | Baumer et al. |
| 7,226,299 B2 | 6/2007 | Pereira et al. |
| 7,366,562 B2 | 4/2008 | Dukesherer et al. |
| 7,395,105 B2 | 7/2008 | Schmidt et al. |
| 2005/0015134 A1 | 1/2005 | Carim |
| 2005/0124902 A1 | 6/2005 | Baumer et al. |
| 2005/0261565 A1 | 11/2005 | Lane et al. |
| 2006/0149146 A1 | 7/2006 | Schmidt et al. |
| 2006/0167354 A1 | 7/2006 | Muller et al. |
| 2007/0016007 A1 | 1/2007 | Govari et al. |
| 2007/0060832 A1 | 3/2007 | Levin |
| 2007/0225593 A1 | 9/2007 | Porath et al. |
| 2008/0114220 A1* | 5/2008 | Banet .................... A61B 5/316 600/382 |
| 2008/0132773 A1 | 6/2008 | Burnes et al. |
| 2008/0288026 A1 | 11/2008 | Cross et al. |
| 2009/0156926 A1 | 6/2009 | Messerly et al. |
| 2009/0227857 A1 | 9/2009 | Rowe et al. |
| 2009/0318793 A1* | 12/2009 | Datta ...................... A61B 5/06 600/391 |
| 2009/0318796 A1 | 12/2009 | Datta et al. |
| 2010/0081913 A1 | 4/2010 | Cross et al. |
| 2011/0021901 A1* | 1/2011 | Gonopolskiy ....... A61B 5/6833 600/391 |
| 2013/0023750 A1 | 1/2013 | Callahan |

FOREIGN PATENT DOCUMENTS

| | | |
|---|---|---|
| JP | 6319712 A | 11/1994 |
| JP | 9131328 A | 5/1997 |
| JP | 10230016 A | 9/1998 |
| JP | 2001506154 A | 5/2001 |
| JP | 2007-61612 A | 3/2007 |
| NL | 1019789 | 7/2003 |
| WO | WO 90/01224 | 2/1990 |
| WO | WO 92/08407 A1 | 5/1992 |
| WO | WO 2007/063436 A1 | 6/2007 |
| WO | WO 2008/068695 A1 | 6/2008 |

OTHER PUBLICATIONS

PCT International Search Report dated Jan. 26, 2010 for PCT/US2009/047995, 7 pages.

Extended European Search Report dated Apr. 23, 2012 for Application No. 11195287.5, 8 pages.

English translation of JPO Office action dated Jul. 3, 2013 for application No. 2011-516477, 3 pages.

Search Report issued by the People's Republic of China dated Mar. 21, 2013 for corresponding Patent Application No. 20098013386.5, English translation, 2 pages.

Japanese Notification of Reasons for Refusal dated Mar. 11, 2014 issued in Japanese Patent Application No. 2011-516477, English translation, 3 pages.

European Search Report for Application No. EP 11178894, dated Oct. 21, 2011, 3 pages.

Extended European Search Report for Application No. EP 12177381.6, dated Oct. 9, 2012, 5 pages.

* cited by examiner

SINGLE RADIO-TRANSPARENT CONNECTOR FOR MULTI-FUNCTIONAL REFERENCE PATCH

CROSS-REFERENCE TO RELATED APPLICATION(S)

This application is a continuation of and claims priority to and the benefit of U.S. patent application Ser. No. 15/194,200 filed Jun. 27, 2016, which is a continuation of and claims priority to and the benefit of U.S. patent application Ser. No. 12/977,881 filed Dec. 23, 2010, issued as U.S. Pat. No. 9,375,179, the entire content of each of which is incorporated herein by reference.

FIELD OF INVENTION

The present invention relates to mechanisms for the attaching a reusable cable and housing containing a biosensor for magnetic field based localization to a conductive and adhesive patch assembly having an electrode used for electrical and mechanical contact with the body surface of a patient. More particularly, the invention relates to a single attachment mechanism between the cable and housing that is optimized for use in an electrophysiology mapping and ablation system using both biosensors and electrodes for magnetic and impedance or current based localization and mapping of medical devices in the human body

BACKGROUND

Many abnormal medical conditions in humans and other mammals have been associated with disease and other aberrations along the lining or walls that define several different body spaces. In order to treat such abnormal conditions of the body spaces, medical device technologies adapted for delivering various therapies to the body spaces using the least invasive means possible.

As used herein, the term "body space," including derivatives thereof, is intended to mean any cavity within the body which is defined at least in part by a tissue wall. For example, the cardiac chambers, the uterus, the regions of the gastrointestinal tract, and the arterial or venous vessels are all considered illustrative examples of body spaces within the intended meaning.

The term "vessel," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of vessels within the intended meaning. Blood vessels are also herein considered vessels, including regions of the vascular tree between their branch points. More particularly, the pulmonary veins are vessels within the intended meaning, including the region of the pulmonary veins between the branched portions of their ostia along a left ventricle wall, although the wall tissue defining the ostia typically presents uniquely tapered lumenal shapes.

One means of treating body spaces in a minimally invasive manner is through the use of catheters to reach internal organs and vessels within a body space. Electrode or electrophysiology (EP) catheters have been in common use in medical practice for many years. They are used to stimulate and map electrical activity in the heart and to ablate sites of aberrant electrical activity. In use, the electrode catheter is inserted into a major vein or artery, e.g., the femoral artery, and then guided into the chamber of the heart that is of concern in order to perform mapping and ablation procedures. It is important to know and be able to map the location of the tip or other portions of such electrode catheters within the vessels or other locations in the body space.

U.S. Pat. Nos. 5,391,199, 5,443,489, 6,788,967 and 6,690,963 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

In United States Patent Application No. 2007/0016007 filed by Govari and incorporated herein by reference, a hybrid position sensing system includes a probe adapted to be introduced into a body cavity of a subject. The probe includes a biosensor having a magnetic field transducer and at least one probe electrodes. A control unit is configured to measure position coordinates of the probe using the magnetic field transducer of the biosensor. The control unit also measures an impedance between the at least one probe electrodes and one or more points on a body surface of the subject. Using the measured position coordinates, the control unit calibrates the measured impedance.

Thus, in such a hybrid magnetic and impedance based systems, a biosensor and electrode must be placed at multiple points on the body surface of the patient. Because the biosensors and the electrical cabling connecting them to the EP mapping system are relatively expensive, it is ideal that the biosensors and the associated cable be reusable. The portion attached to the skin is preferably disposable, therefore, a disposable patch is necessary for affixing the reusable biosensor and possibly a portion of the electrode to the skin of the patient.

Existing patches comprises one or more stainless steel studs, foam and a conductive adhesive gel that is in contact with the skin of the patient. The matching patch cable in existing systems primarily comprise one or more matching stainless steel snaps into which the studs of the patch mate, a biosensor and the associated electrical cable all housed in an epoxy shell. Existing biosensor cable and patch mechanisms are radiopaque, i.e., the stainless steel snaps and studs appear on fluoroscopy. When multiple snaps are used which is often the case in order to provide a secure and non-rotating connection between the patch and the sensor cable, the multiple snaps do not allow the patch to take the shape of the body. Also, the patches are often large and conflict with other patches used on the body for ECG, defibrillators, intra-cardiac echograms, etc.

Notably, U.S. Pat. No. 3,606,881, relates to a disposable patch having a metallic terminal with an enlarged head which permits a squeeze activated clip to be secured around the metallic terminal. U.S. Pat. No. 3,829,826 provides a mechanical mechanism for attaching to the standard male metallic snap of the standard ECG patch. U.S. Pat. No. 4,490,005 relates to a patch in which the central stud is a metal coated non-metallic substrate and which permits rotation of the sensor cable while reducing the effect of rotation on the metal to metal connection. U.S. Pat. No. 4,635,642 relates to a disposable pad in which a conductive, preferably, silver coated metallic stud is inserted in order to make electrical conduct with a gel matrix that is in contact with the skin of the patient.

A similar conductively coated electrically conductive plastic is provided in U.S. Pat. No. 5,499,628 as an eyelet that is press fit into a terminal made of a resilient nonmetallic composition such as polypropylene blended with carbon fiber. Additionally, U.S. Pat. No. 5,615,674 relates to a clamping contact connection for contacting a fetal scalp probe. U.S. Pat. No. 5,782,761 relates to a molded electrode one-piece and two-piece constructions for a molded electrode made of a conductive material such as a carbon-filled plastic. U.S. Pat. No. 6,650,922 relates to an electrode element made of an electrode made of a biodegradable material that is also electro conductive. U.S. Pat. No. 6,780,065 relates to a device for electrical connection of the power lead to an electrode for use on the skin. U.S. Pat. No. 7,226,299 relates to a circular electrical connector that engages the socket of a female connector that may include a locking device having resilient prongs. Design Pat. 240,166 relates to a medical electrode with a rectangular cube portion. U.S. Patent Application Publication No. 2006/0167354 relates to a system for connecting an electrode to a conductive cable. U.S. Patent Application Publication No. 2006/0149146 relates to a device having an electrode for contact with the patient and a pressure sensor. U.S. Pat. No. 5,978,693 relates to an electrode having a deformation sensor such as a strain gauge.

U.S. patent application Ser. No. 12/256,580, now U.S. Patent Publication No. 2009/0318793, the entire disclosure of which is hereby incorporated by reference, relates to a patch and sensor assembly with a disposable portion and a reusable portion, each having a respective cable for connection to a mapping and localization system.

It is an object of the present invention to provide a patch that is generally not visible under fluoroscopy. It is a further object of the present invention that the patch be capable of being smaller than currently used patches so as to minimize the amount of space used on the skin of the patient and reduce potential conflict with other patches. Additionally, it is an object of the present invention to provide a patch and sensor cable that will not rotate as would previous designs utilizing a single snap. Furthermore, it is an object of the present invention to have a patch and sensor cable attachment mechanism that is easy to attach. Additionally, it is an object of the present invention to have a patch and sensor cable design that could be used for ECG or other instrument systems. Moreover, it is an object of the present invention to have a patch and sensor cable attachment mechanism that enables repeated reuse of the biosensor and sensor cable without any degradation in performance. Finally, it is an object of the present invention to provide a single cable attachment for both the biosensor and electrode of a given patch.

SUMMARY OF THE INVENTION

The present invention generally relates to a radio-transparent patch and sensor assembly for use in an electrophysiology mapping and ablation system, in which the assembly includes a reusable portion and a disposable portion in which the reusable portion is releasably engaged. More specifically, the present invention relates to a patch and sensor assembly in which a magnetic-based biosensor is housed in the reusable portion that connects to the mapping and localization system via biosensor wires, and the disposable portion provides an electrode layer through which impedance-based signals are transmitted to the mapping and localization system via ACL (active current location) wires, wherein the biosensor wires and the ACL wires extend through a single cable exiting the reusable portion.

In one embodiment, the disposable portion includes an adhesive layer for adhering the electrode layer to a patient's body where the electrode layer is disposed on the adhesive hydrogel layer. The disposable portion also includes a foam layer disposed on the electrode layer, and an engagement element adapted to detachably receive at least a portion of a housing of the reusable portion.

In one embodiment, the reusable portion includes a housing defining a sealed interior volume in which a magnetic-based biosensor is provided with biosensor wires that exit the reusable portion. The housing is also adapted to carry and/or provide support to an ACL contact member that is responsive to the electrode layer of the disposable portion, and ACL wires for the ACL contact member that exit the reusable portion. Advantageously, the biosensor wires and the ACL wires extend through a single cable to a mapping and localization system.

In a more detailed embodiment, the disposable portion provides at least an electrode that electrically couples the electrode layer and a patient-facing ACL contact member when the reusable portion is detachably engaged with the disposable portion. In another more detailed embodiment, the disposable portion provides a flexible circuit member with electrically conductive contact members that couple the electrode layer and an away facing ACL contact member when the reusable portion is detachably engaged with the disposable portion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
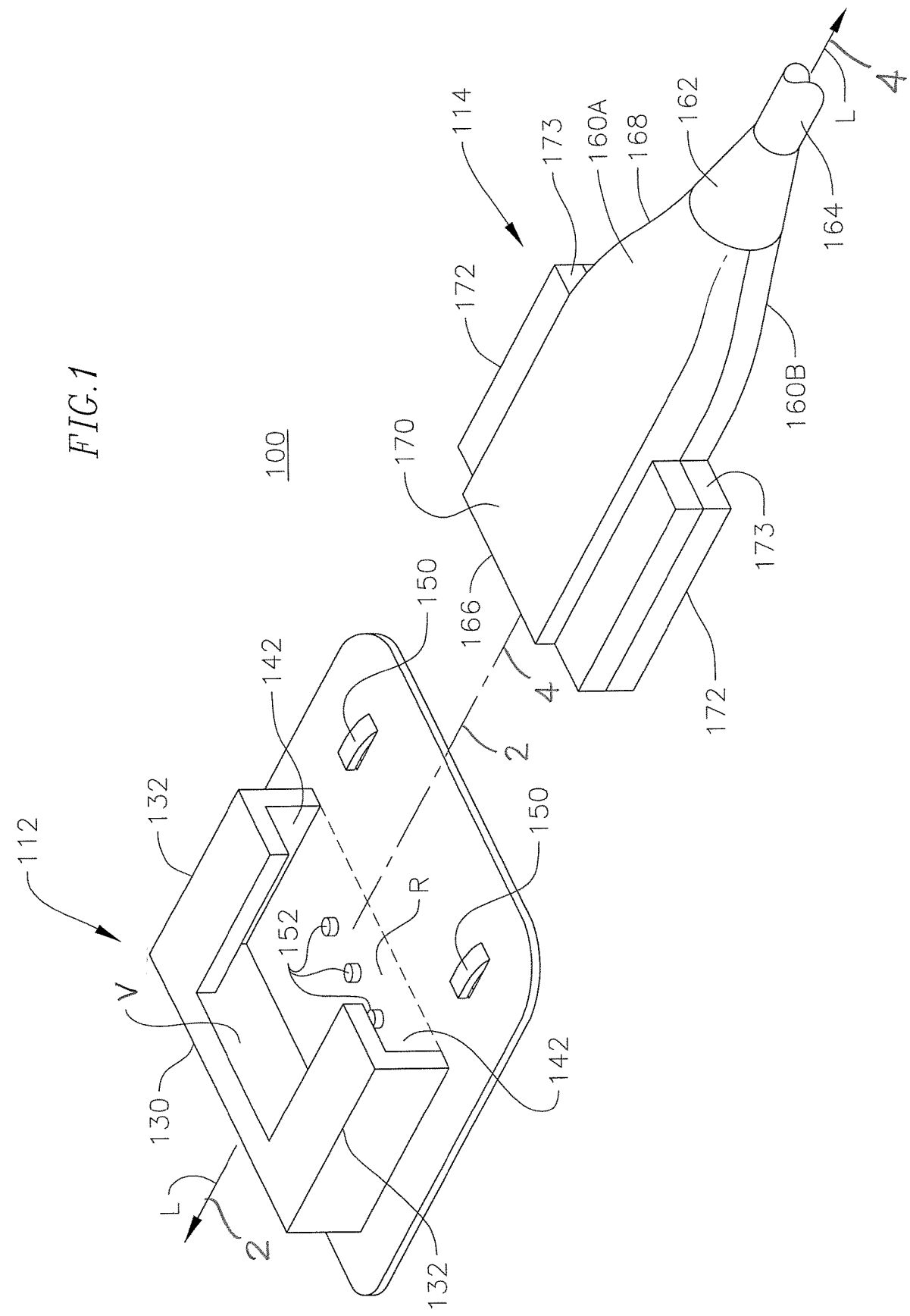
FIG. 1 is a perspective view of a patch and sensor assembly in accordance with an embodiment of the present invention.

Referring to the drawings, FIG. 1 depicts an embodiment of a single-cable patch and cable assembly 100 in accordance with the present invention. As shown in FIG. 1, the patch and cable assembly 100 comprises two major components: a patch connector assembly 112 and a sensor cable assembly 114. The sensor cable assembly 114 is inserted and releasably received in the patch connector assembly 112 so that signals representative of a position of the coupled patch and cable assembly 100 generated by a magnetic field transducer and at least one probe electrode are transmitted to a control unit via a single cable.

Figure 2:
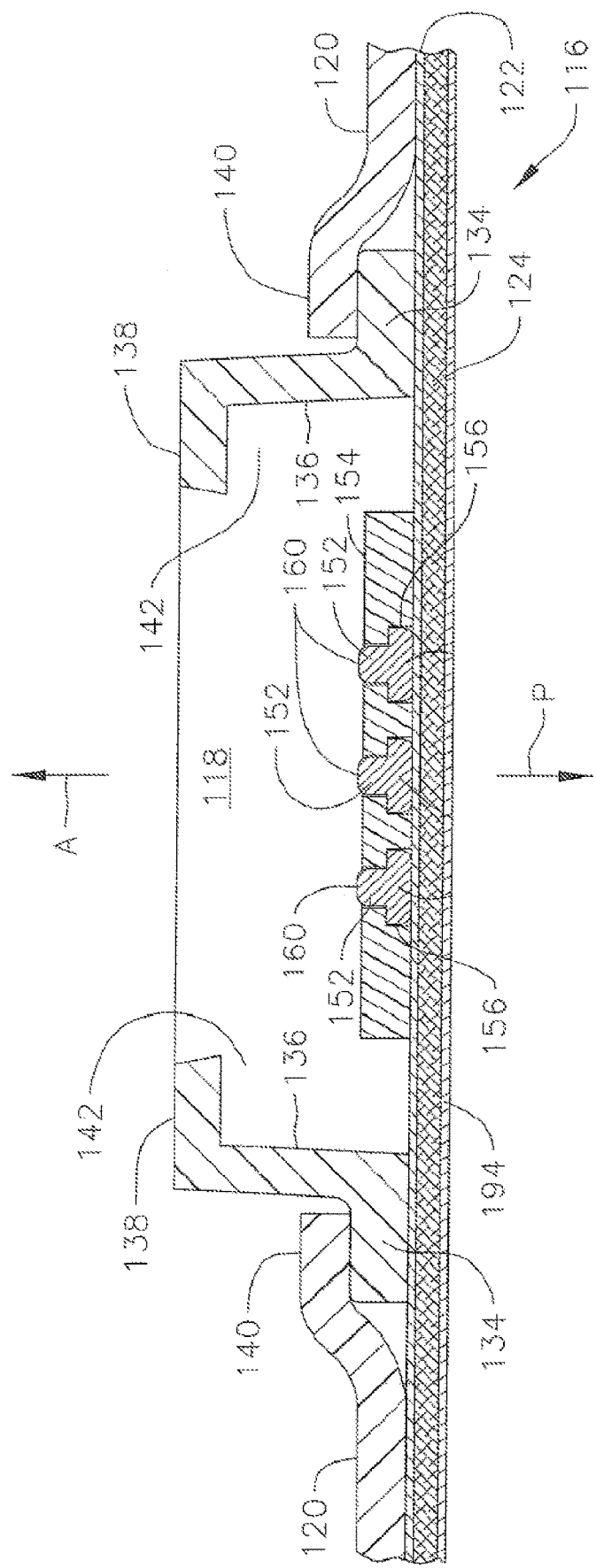
FIG. 2 is a cross sectional view of a disposable patch connector assembly of FIG. 1 taken along line 2-2.

As also shown in FIG. 2, the patch connector assembly 112 includes a lower patch portion 116 and an upper connector portion 118. The lower patch portion includes a foam layer 120 resting above a conductive electrode layer, for example, carbon film 122 coated with a layer of silver chloride on both sides. The foam used to form foam layer may be any suitable material such as thermofoam, any elastomers like rubber, santoprene, polyurethane etc. and is preferably thermofoam. The carbon film 122 is about 0.5 mm in thickness and the layer of silver chloride is about 0.1 mm in thickness. Other thicknesses of carbon film and silver chloride coating may be used as suitable. On a patient facing side of the carbon film is a hydrogel layer 124 including a conductive gel medium, which also has adhesive properties to the skin, preferably a hydrogel being a mix of silver/silver chloride (Ag/AgCl) with water based compound and having a thickness of about 1.0 mm. The foam layer 120, the carbon film 122 and the hydrogel layer 124 generally have approximately the same size which should be large enough to provide a secure attachment to a body surface of the patient and is preferably between 4 cm$^2$ and 16 cm$^2$.

With reference to FIGS. 1 and 2, the connector portion 112 is adapted to receive a distal portion of the sensor cable assembly. In the disclosed embodiment, the connector portion has a size and shape corresponding to the distal portion of the sensor cable assembly in defining a receiving area R on the surface of the patch portion facing away from the patient (designated A in FIG. 2) and a receiving volume V thereabove. The shape of the connector portion 118 is generally rectangular, preferably a U-shape with a mid-portion 130 that is transverse to a longitudinal axis L of the assembly 100, and two side portions 132 that are parallel to the longitudinal axis. As better shown in FIG. 2, each portion has a bottom flange 134 that extends outwardly and generally parallel with the away side (A) of the patch portion 116 and is secured to the patch portion by a surrounding edge 140 of the foam layer 120 of the patch portion. Extending generally perpendicularly from the bottom flange of each portion (and thus from the plane of the patch portion 116) is a main wall 136 of the connector portion 118. Each of the two side portions 132 also has a top flange 138 that extends inwardly toward each other. Each top flange and its respective side portion effectively form a slot 142. The connector portion can be made of any suitable material, including, for example, a polymer such as ABS, nylon, polypropylene or other suitable polymer known in the art and is preferably made from polypropylene. Aligned with and a predetermined distance from each slot is a stop 150 configured from the foam layer 120. In the disclosed embodiment, the stop 150 is a cut or notched portion of the foam layer that forms a raised formation on the away side (A) of the patch. It is understood that other materials may be used for the stops but by using existing materials such as the foam layer, the cost of manufacturing is reduced to promote disposability.

Figure 3:
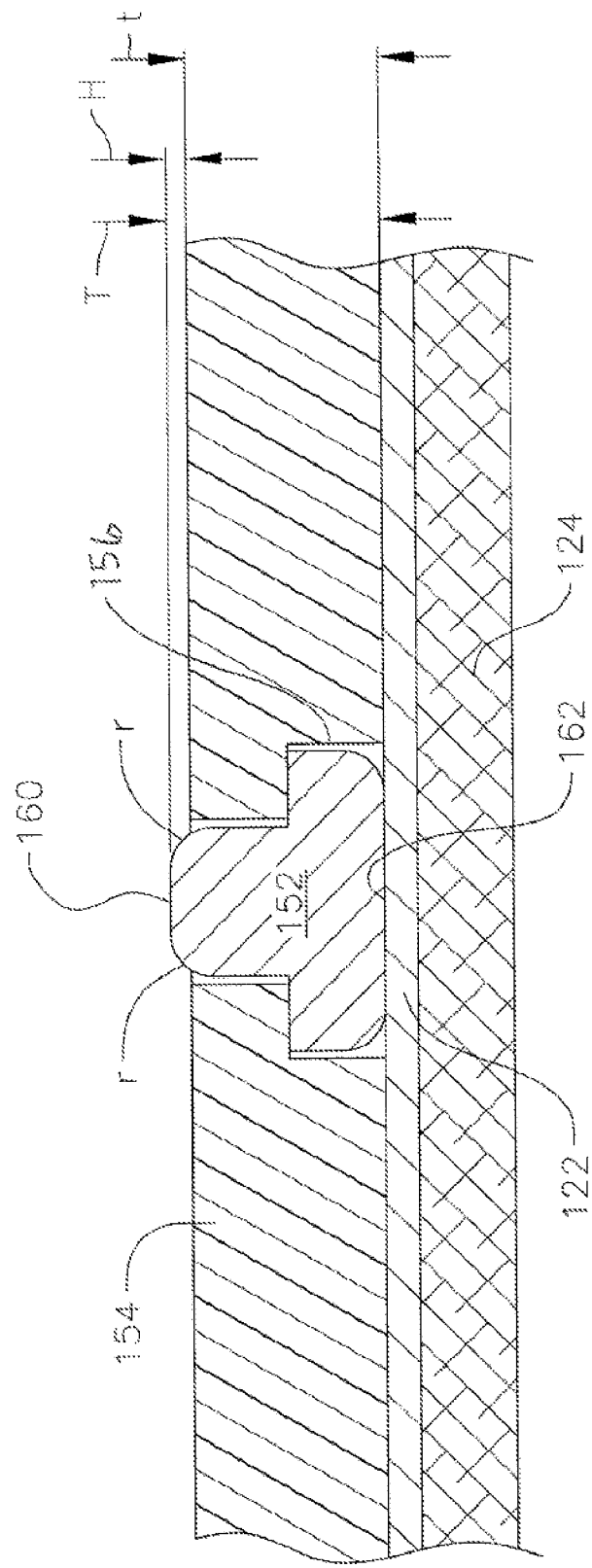
FIG. 3 is a detailed cross-sectional view of an electrode of the disposable patch connector assembly of FIG. 2.

In the receiving area R of the patch portion 116, there are provided a plurality of electrode members 152, for example, about two to six, or three protruding floating carbon electrode pins, nested in a contact member or plate, for electrically coupling between the patch connector assembly 112 and the sensor cable assembly 114. The contact plate 154 can be made of any suitable material but preferably of the same material as the connector portion 118. In the illustrated embodiment of FIG. 3, each pin has a T-shape (with a smaller exposed end 160 adapted to make contact with the sensor cable assembly 114) that is closely received in a corresponding T-shaped opening 156 formed in the contact plate 154. Notably, length T of the electrode pins 152 is greater than a thickness t of contact plate 154 so that the smaller exposed end 160 of the pins protrude a height H beyond the contact plate 154 whereas a larger proximal end 162 contacts and abuts the carbon film 122. The exposed distal end of the pins 152 has a rounded profile, r, with a radius that is sufficiently large to facilitate insertion of the sensor cable assembly 114 into the connector portion 118. The height H of the exposed distal end ensures contact between the sensor cable assembly 114 and the electrode pins 152. The T-shaped cross section of the openings 156 retains the electrode pins within the openings. The hydrogel layer 124 being generally elastic provides resistance for the electrode pins 152 and thus behaves as a spring which ensures contact between the pins and the sensor cable assembly 114 while minimizing wear and tear to both. Advantageously, the patch connector assembly 112 uses a minimal number of components, most if not all of which are low-cost, in order to increase its disposability in this embodiment.

Figure 4:
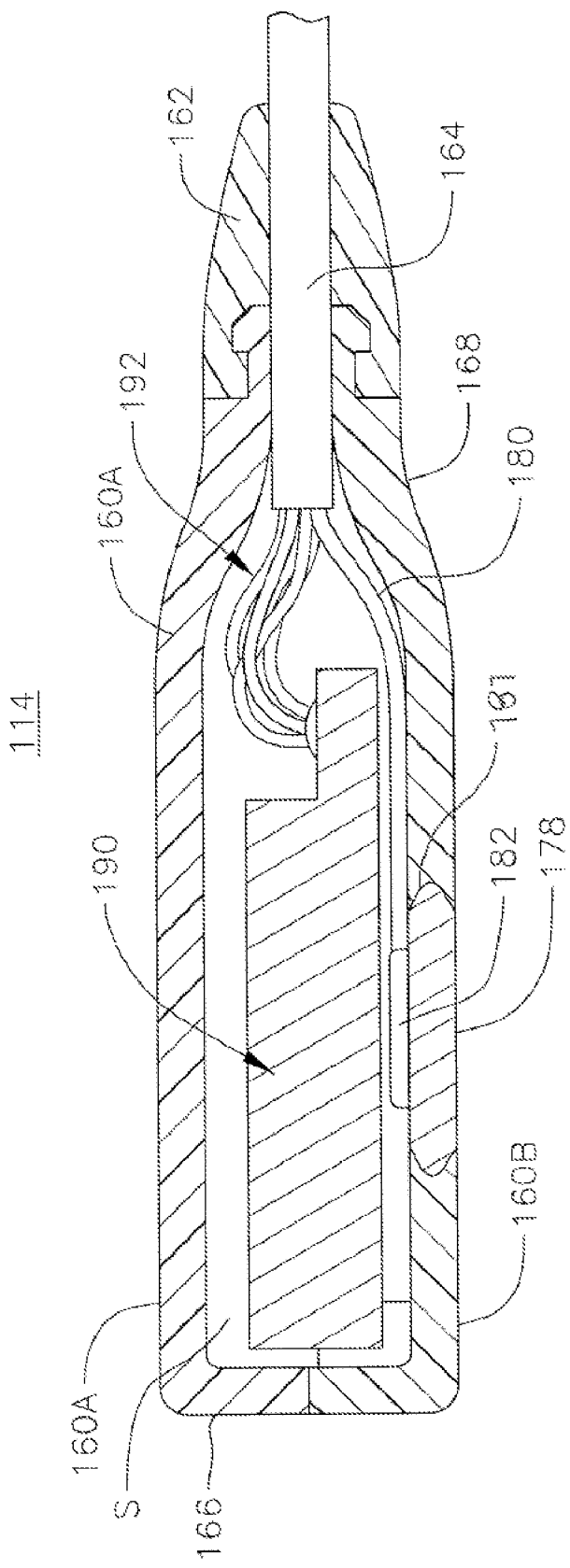
FIG. 4 is a side cross-sectional view of a reusable sensor cable assembly of FIG. 1 taken along line 4-4.

As shown in FIG. 4, the reusable sensor cable assembly 114 has a housing 160 that provides an enclosed and sealed interior volume or space S. In the disclosed embodiment, the housing includes a first and top housing 160A and a second and bottom housing 160B. The sensor cable assembly also preferably includes a strain relief element 162 at the proximal end of the housing. Strain relief element 162 may be integral with sensor housing 160 or may comprise a separate polymeric sleeve that covers a portion of single cable 164. Suitable housing materials include a polymer such as ABS, nylon, polypropylene or other suitable polymer known in the art and is preferably made from polyproplylene. In the illustrated embodiment, the housing 160 is elongated with a generally rectangular distal section 166 and a tapered proximal section 168. As better shown in FIG. 1, the distal section has a main thicker portion 170 and two smaller thinner side portions 172 extending laterally from the main portion. The distal section 166 is inserted into the receiving volume V of the connector portion 118 of the patch connector assembly 112.

With reference to FIG. 4, the bottom housing 160B provides a generally flat surface for generally planar contact with the patch connector assembly 112. The bottom housing includes a contact member 178 for electrical connection between the patch connector assembly 112 and the sensor cable assembly 114. The contact member 178 can be made of any suitable conductive material. In the disclosed embodiment, the contact member 178 includes an active current location (ACL) sensor nested in a through-hole or opening 181 formed in the bottom housing 160b. The ACL sensor may be made of a suitably conductive material and is preferably a generally circular carbon disk coated with silver chloride. Gold or platinum may also be used instead of silver chloride for the coating and the carbon disk could be replaced with a polymer such as ABS or polycarbonate with or without carbon fibers embedded therein. An ACL conductor or wire 180 is attached to the ACL sensor by means of a suitable conductive epoxy 182, preferably any epoxy preferably embedded with silver particles.

Figure 5:
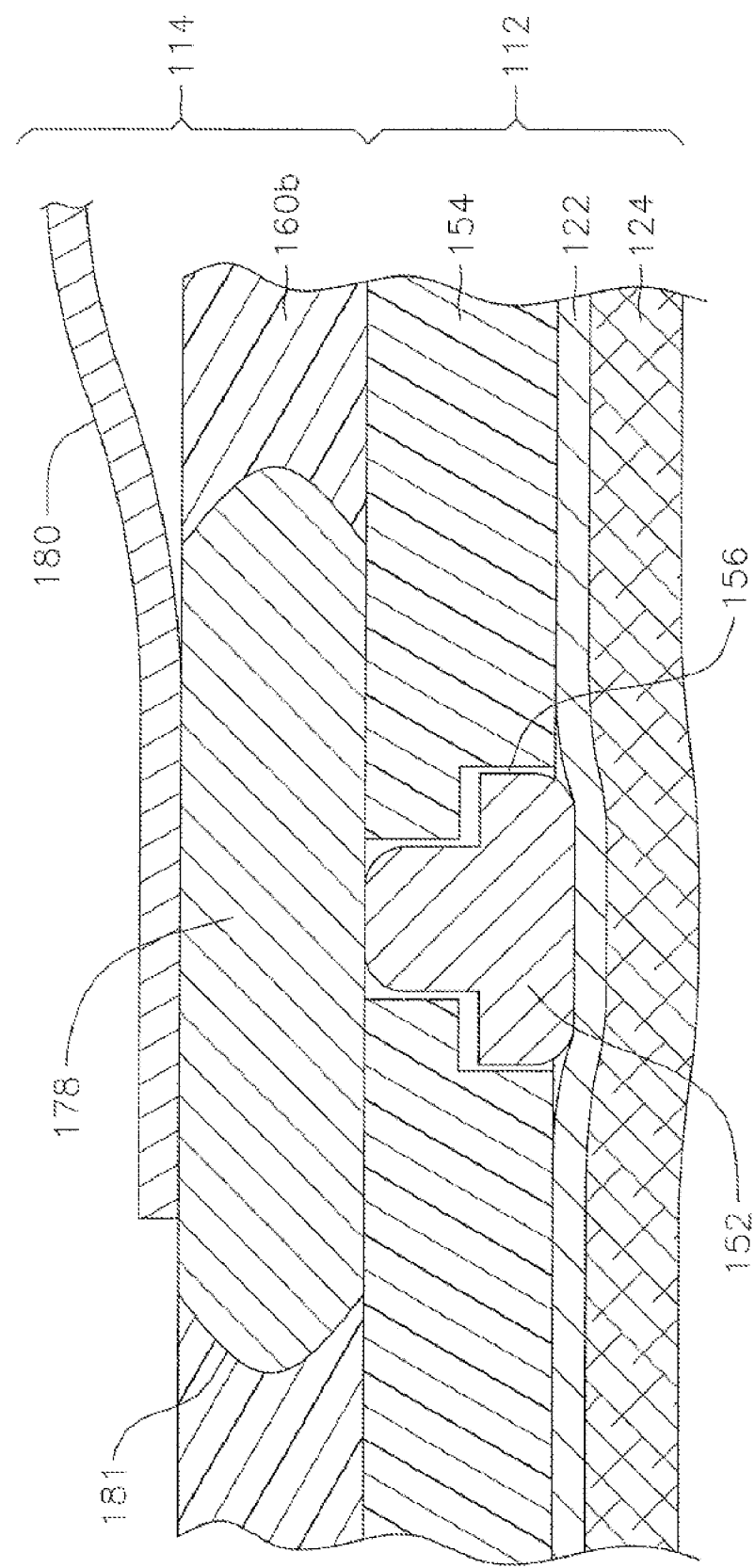
FIG. 5 is a detailed cross-sectional view of the electrode of FIG. 3 when depressed when the reusable sensor cable assembly is detachably engaged with the disposable patch connector assembly.

With reference to FIG. 5, in use, current flowing through the patient is conducted through the hydrogel layer 124, the carbon film 122, the electrode pins 152, the ACL sensor 178, the ACL wire 180 which transmits signals to the localization and mapping system that uses the ACL information to perform localization and mapping functions in accordance with US Patent Application No. 2007/0016007 filed by Govari, the entire content of which is incorporated herein by reference, or other such similar system.

As shown in FIG. 4, housed in the interior space S of the sensor cable assembly 114 is a magnetic-based biosensor 190 that is connected to the mapping and localization system via a plurality of sensor conductors or wires 192. The biosensor is implemented in accordance with one or more of U.S. Pat. Nos. 5,391,199, 5,443,489, 6,788,967 and 6,690,963 to Ben-Haim, whose entire disclosures are incorporated herein by reference. Magnetic field based information from the biosensor is an electrical current induced by a magnetic field in which the patient is placed and is used in a manner similar to that used in the CARTO™ EP mapping systems manufactured and sold by Biosense Webster, Inc. The electrical current from the biosensor is conducted through three twisted pair conductor wires 192 of the sensor cable which connects to an EP mapping and localization system where the information is used. An isolation layer, for example, a thin piece of plastic material preferably polypropylene, ABS or polycarbonate, or potting around the ACL wire can be provided between the ACL sensor and the biosensor to isolate the 4 KV defibrillation pulse from ACL wire to the biosensor.

Advantageously, the biosensor 190 is positioned proximately to the ACL sensor 178 for greater accuracy in location sensing. In the disclosed embodiment, the biosensor is positioned centered and directly above the ACL sensor. The single cable 164 exiting the sensor cable assembly 114 thus includes the conductive ACL wire 180 made of a conductive and flexible material, preferably 28 gauge braided copper wire for the ACL sensor 178, and three twisted pair conductor wires 192 for the biosensor 190, along with two KEVLAR fibers for added strength inside a polymeric outer sheath. One wire in the sensor cable is welded or bonded to the biosensor using a conductive epoxy.

In use, a release liner 194 (FIG. 2) is removed from the patient-facing side (P) of the patch connector assembly 112 to expose the hydrogel layer 124 for adhesion to the skin of a patient. The sensor cable assembly 114 is then inserted into the connector portion 118 on the patch connector assembly 112 with the distal end 166 being received in the connector portion such that each side member 172 is received in a respective slot 142 and the main body 170 of the upper housing is exposed between the two top flanges 138 of the connector portion 118. A proximal end 173 of each side member is releasably wedged against a respective stop 150 on the away side (A) of the patch portion 116. As shown in FIG. 5, contact between the contact member 178 and the floating electrodes 152 is ensured by the elastic hydrogel layer 124 such that electrical impedance signals from the patient's body are transmitted through the electrode pins 152 and the ACL sensor 178 and further transmitted through the ACL wire 180 extending through the single cable 164. Magnetically-based position signals from the biosensor 190 are transmitted through the biosensor wires 192 also extending through the single cable 164.

Figure 6:
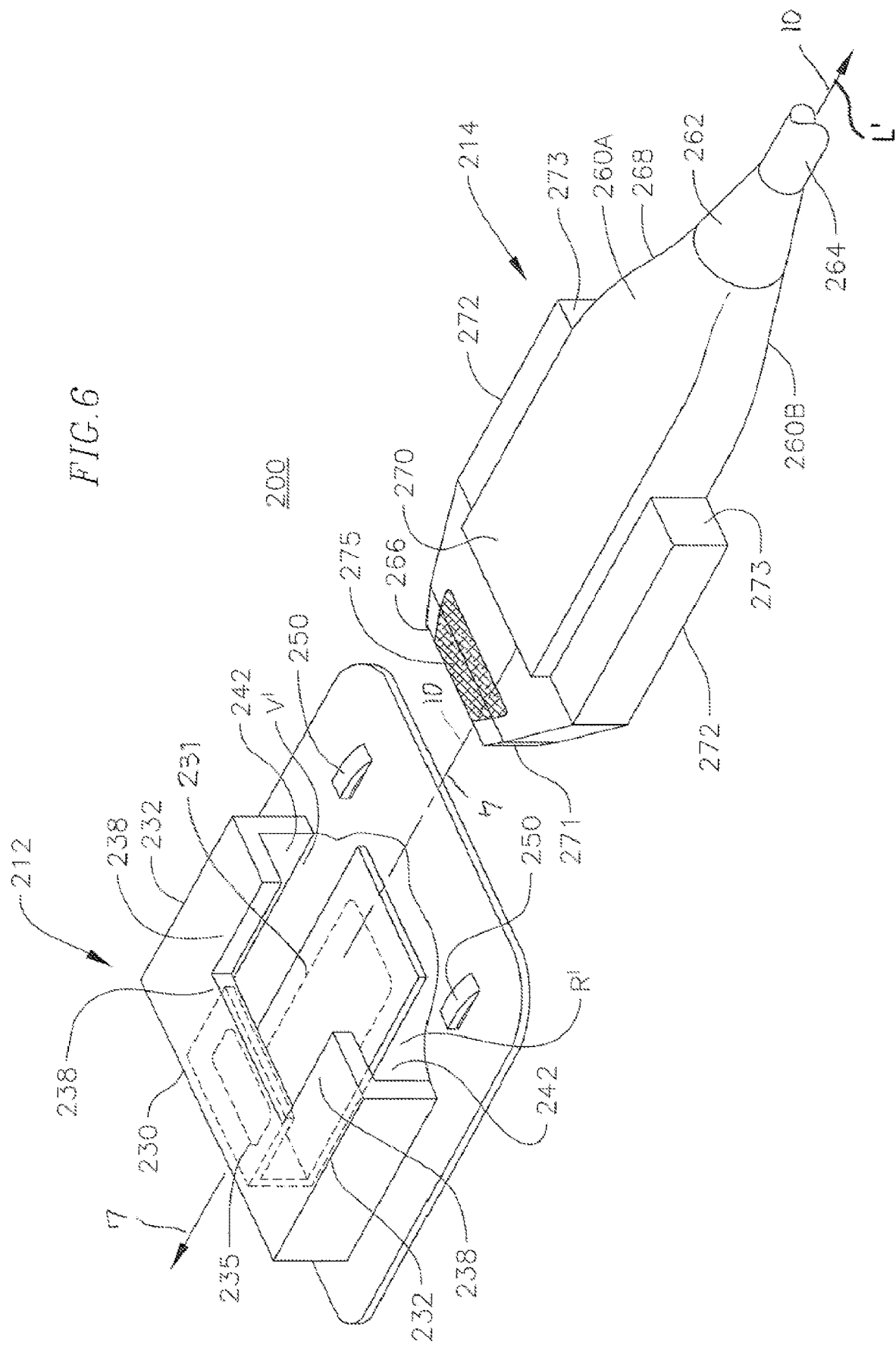
FIG. 6 is a perspective view of a patch and sensor assembly in accordance with an alternate embodiment of the present invention.

FIGS. 6-10 depict an alternate embodiment of a single-cable patch and cable assembly 200 in accordance with the present invention. The assembly 200 has many similarities to the aforementioned assembly 100, but there are differences, including those as follow. As shown in FIG. 6, the patch and cable assembly 200 comprises two major components: a patch connector assembly 212 and a sensor cable assembly 214. The sensor cable assembly 214 is inserted and releasably received in the patch connector assembly 212 so that signals representative of a position of the coupled patch and cable assembly generated by a magnetic field transducer and at least one probe electrode are transmitted to a control unit via a single cable 264.

Figure 7:
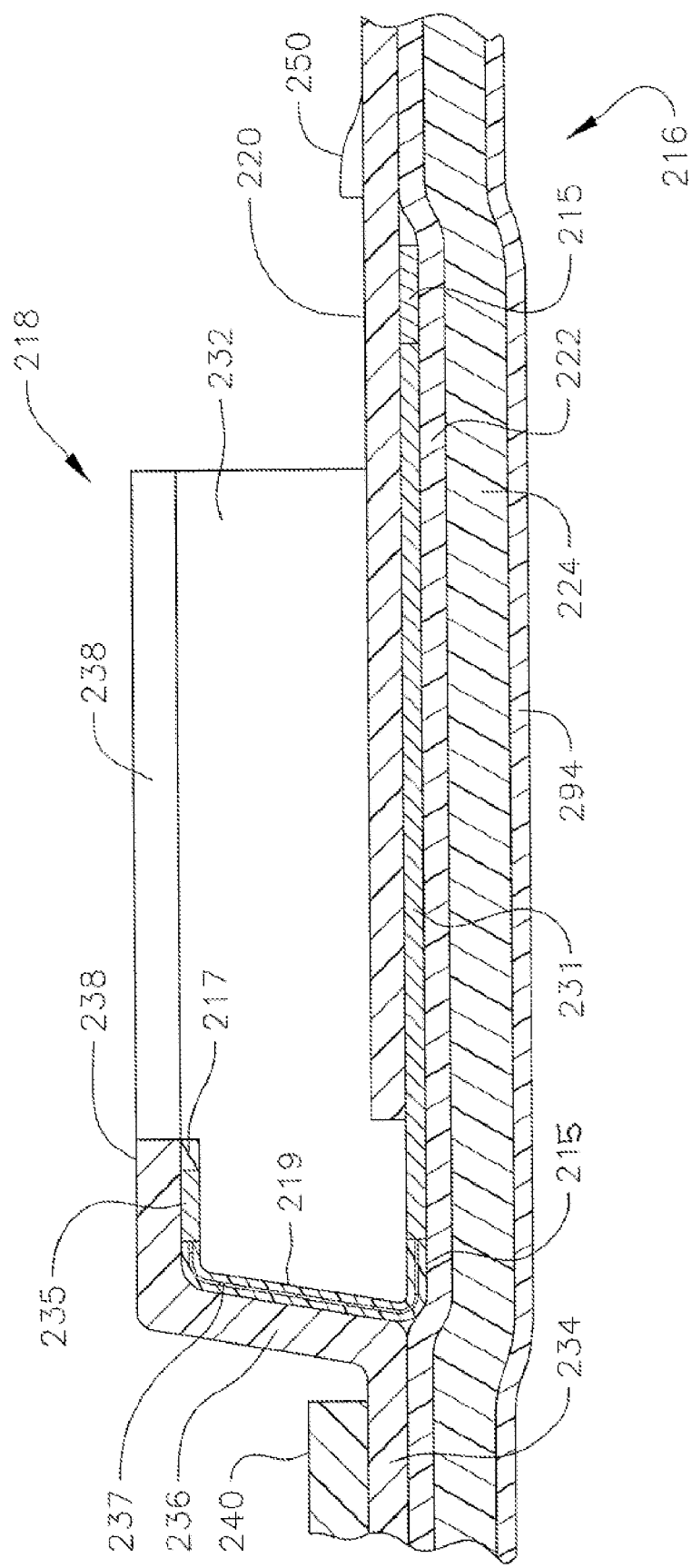
FIG. 7 is a side cross-sectional view of a reusable sensor cable assembly of FIG. 6 taken along line 7-7.
Figure 8:
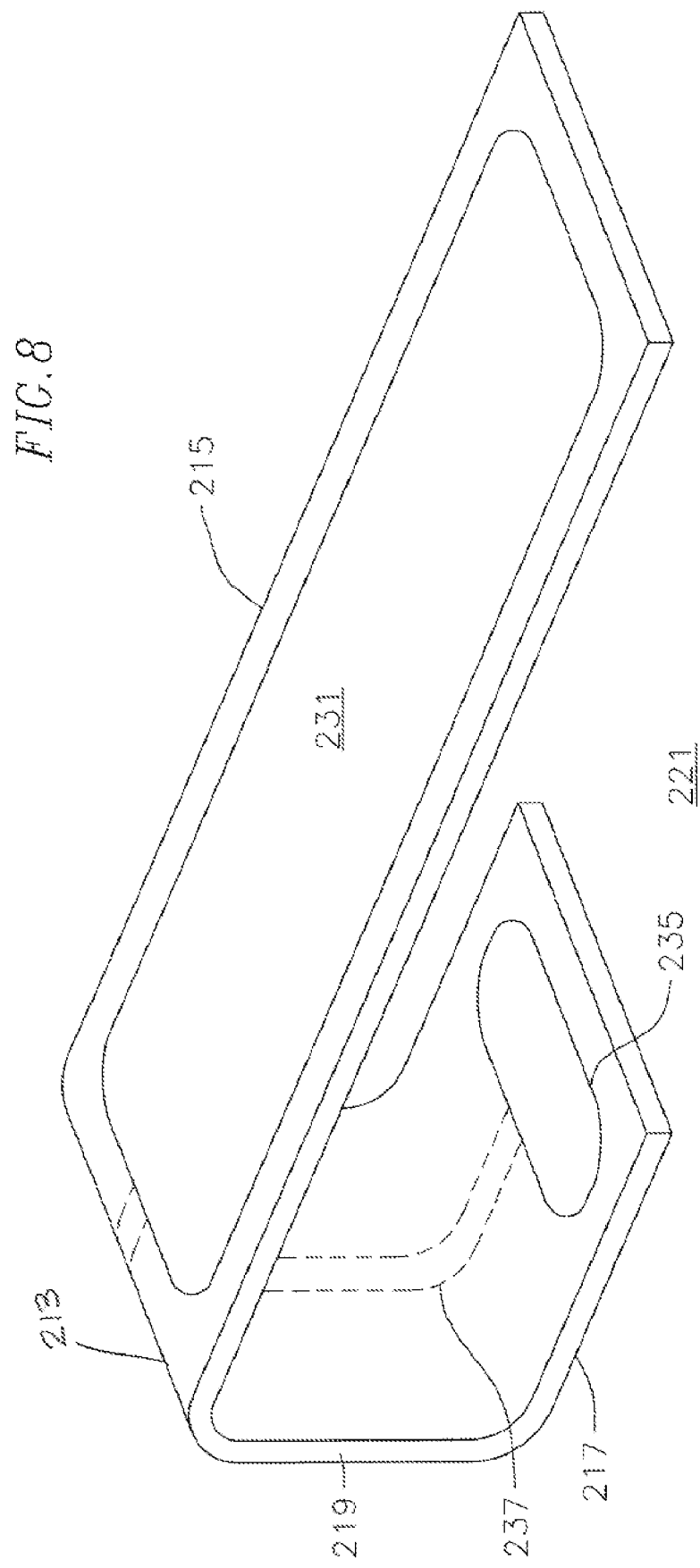
FIG. 8 is a perspective view of a flexible circuit member in accordance with one embodiment of the present invention.

As shown in FIGS. 7 and 8, the patch connector assembly includes a lower patch portion 216, an upper connector portion 218, and a circuit member 221, for example, a flex circuit substrate. The patch portion includes a foam layer 220 resting above a conductive electrode layer, for example, a carbon film 222 coated with a layer of silver chloride on both sides. The foam used to form foam layer 220 may be any suitable material such as thermofoam, any elastomers like rubber, santoprene, polyurethane etc. and is preferably thermofoam. The carbon film is about 0.5 mm in thickness and the layer of silver chloride is about 0.1 mm in thickness. Other thicknesses of carbon film and silver chloride coating may be used as suitable. On a patient facing side of the carbon film 222 is a hydrogel layer 224 including a conductive gel medium, which also has adhesive properties to the skin, preferably a hydrogel being a mix of silver/silver chloride (Ag/AgCl) with water based compound and having a thickness of about 1.0 mm.

The connector portion 218 is adapted to receive a distal portion 266 of the sensor cable assembly 214. In the disclosed embodiment, the connector portion has a size and shape corresponding to the distal end of the sensor cable assembly in defining a receiving area R' on the away surface of the patch portion 216 and a receiving volume V' thereabove. The shape of the connector portion 218 is generally rectangular, preferably a U-shape with a mid-portion 230 that is transverse to a longitudinal axis L' of the assembly 200, and two side portions 232 that are parallel to the longitudinal axis. Each portion has a bottom flange 234 that extends outwardly and generally parallel with the away side of the patch portion and is secured to the patch portion 216 by a surrounding edge 240 of the foam layer 220 of the patch portion 216. Extending generally perpendicularly from the bottom flange of each portion (and thus from the plane of the patch portion) is a main wall 236 of the connector portion 218. Each portion also has a top flange 238 that extends inwardly toward each other. The three top flanges and their respective side portions effectively form a U-shaped slot 242. The connector portion can be made of any suitable material, including, for example, a polymer such as ABS, nylon, polypropylene or other suitable polymer known in the art and is preferably made from polypropylene. Aligned with and a predetermined distance from each slot is a stop 250 configured from the foam layer 220. In the disclosed embodiment, the stop is a cut or notched portion of the foam layer that forms a raised formation above the away side of the patch. It is understood that other materials may be used for the stops but by using existing materials such as the foam layer, the cost of manufacturing is reduced to promote disposability.

As shown in FIG. 8, the circuit member 221 has a flexible substrate body 213 that is elongated and generally U-shaped so that it molds and fits inside of the connector portion 218 within the receiving volume V'. The substrate body has opposing longer leg 215 and shorter leg 217 that extend parallel to each other and perpendicularly from a midsection 219. The longer leg 215 lies on the away side of the patch portion 216. The mid-section 219 lies along an inner surface of the main wall 236 of the mid portion 230. The shorter leg 217 lies along an inner surface of the top flange 238 of the mid portion 230. The longer leg 215 has a patch contact pad 231 that contacts the carbon film 222 of the patch portion 216. The shorter leg 217 on its patient-facing side has an ACL connector contact patch 235. Extending between the patch contact pad 231 and the ACL connector contact patch 235 is a conductor element 237 for electrically coupling the pad and the patch. The patch contact pad 231, the ACL connector contact patch 235 and the conductor element 237 are of gold or other material suitable for creating traces in a flex circuit. The away side of the longer leg 215 is a covered, protected and electrically insulated by the foam layers 220 (which is shown partially broken away in FIG. 6).

Figure 9:
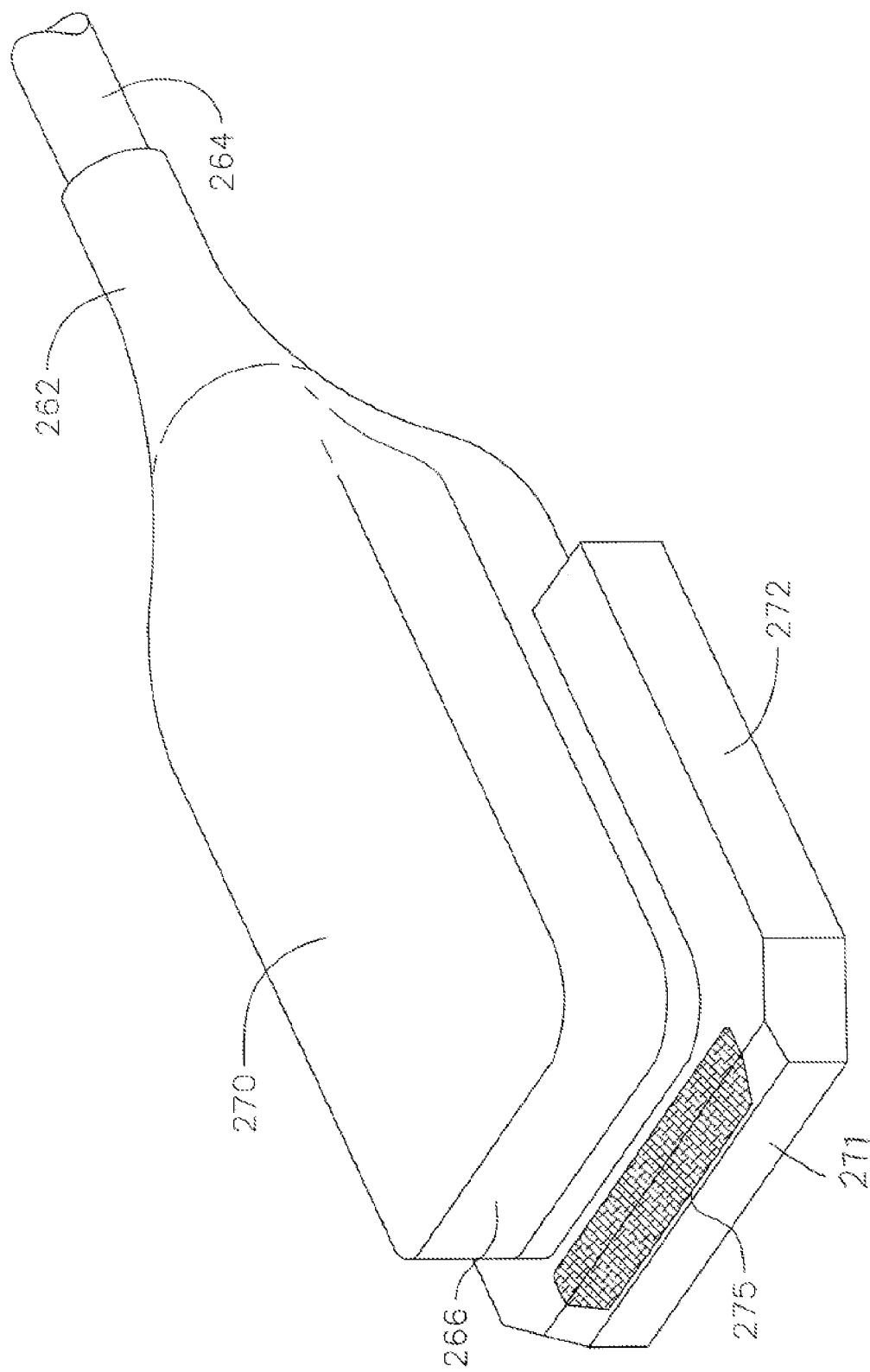
FIG. 9 is a perspective view of the reusable sensor cable assembly of FIG. 6.
Figure 10:
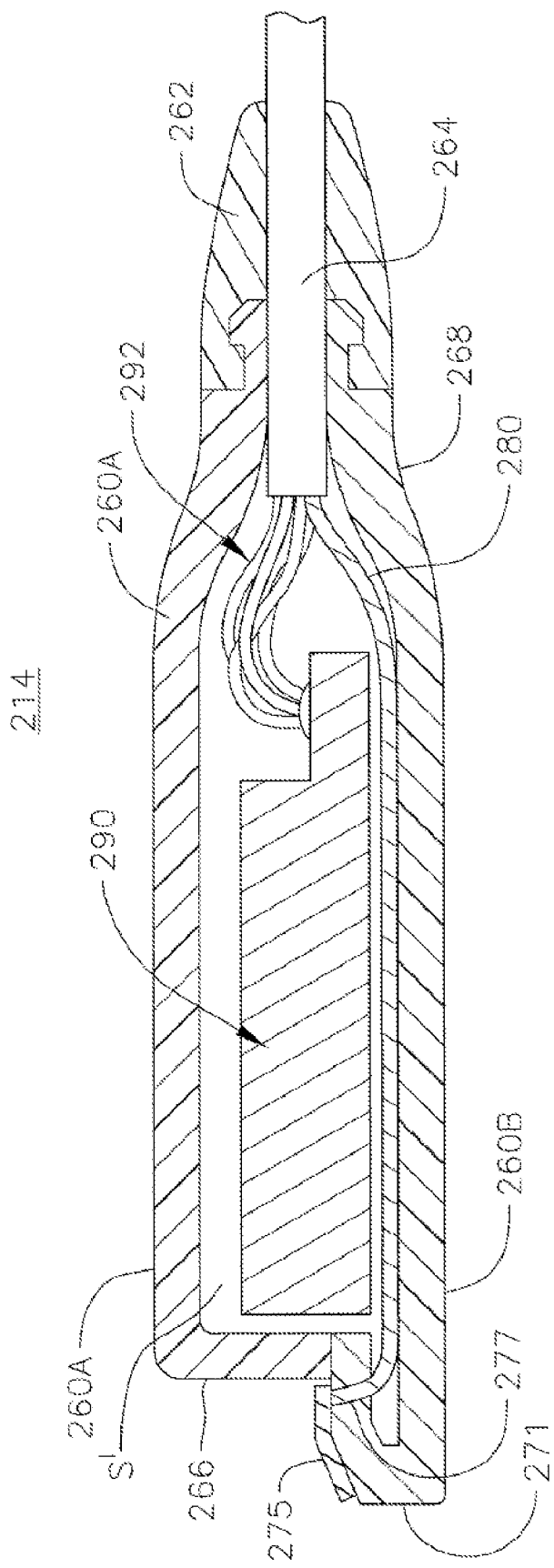
FIG. 10 is a side cross-section view of the reusable sensor cable assembly of FIG. 6 taken along line 10-10.

As shown in FIG. 9, the reusable sensor cable assembly 214 has a housing 260 that provides an enclosed interior volume or space S'. In the disclosed embodiment, the housing includes a first and top housing 260A and a second and bottom housing 260B. The sensor cable assembly 214 referably includes a strain relief element 262 at the proximal end of the housing. Strain relief element 262 may be integral with sensor housing or may comprise a separate polymeric sleeve that covers a portion of sensor cable 264. Suitable housing materials include a polymer such as ABS, nylon, polypropylene or other suitable polymer known in the art and is preferably made from polyproplyene. In the illustrated embodiment, the housing is elongated with a generally rectangular distal section 266 and a tapered proximal section 268. The distal section has a main thicker portion 270 and two smaller thinner side portions 272 extending laterally from the main portion. The distal section 266 of this embodiment has a protrusion or chin portion 271 that provides an away-facing surface on which an ACL contact pad 275 is provided to make contact with the patient-facing ACL connector contact pad 235 of the circuit member 221 when the distal section 266 is inserted into receiving volume V' of the connector portion 218 of the patch connector assembly 212. The ACL wires are attached to the ACL contact pad 275 by means of a suitable conductive epoxy, preferably any epoxy preferably embedded with silver particles, via an aperture 277 formed in the chin portion 271 of the bottom housing 260B.

In use, current flowing through the patient is conducted through the hydrogel layer 224, the carbon film 222 to the patch contact pad 231 of the flex circuit member 221, through trace conductor 237, to the ACL connector contact pad 235, the ACL contact pad 275 and to the ACL wires 280 to the localization and mapping system that uses the ACL information to perform localization and mapping functions in accordance with US Patent Application No. 2007/0016007 filed by Govari, the entire content of which is incorporated herein by reference, or other such similar system.

Housed in the interior space S' is a magnetic-based biosensor 290 that is connected to the mapping and localization system via a plurality of sensor wires 292, as described above. An isolation layer (not shown), for example, a thin piece of plastic material preferably polypropylene, ABS or polycarbonate, or potting around the ACL wire can be provided between the ACL sensor wire and the biosensor to isolate the 4 KV defibrillation pulse from ACL wire to the biosensor.

Again, the biosensor is positioned proximately to the ACL sensor for greater accuracy in location sensing. A single cable exiting the sensor cable assembly 214 is provided which includes a conductive ACL conductors or wires 280 made of a conductive and flexible material, preferably 28 gauge braided copper wire, for the ACL contact pad 275 and three twisted pair conductors or wires 292 for the biosensor 290, along with two KEVLAR fibers for added strength inside a polymeric outer sheath. One wire for the sensor is welded or bonded to the biosensor using a conductive epoxy.

In use, a release liner 294 (FIG. 7) is removed from the patch connector assembly 212 to expose the hydrogel layer 224 for adhesion to the skin of a patient. The sensor cable assembly 214 is then inserted into the connector portion 218 on the patch connector assembly with the distal end 266 and the chin portion 271 being received in the connector portion 218 such that each side member 272 is received in a respective slot 242 and the main body 270 of the upper housing 260A is exposed between the three top flanges 238 of the connector portion 218. A proximal end 273 of each side member is wedged against a respective stop 250 on the away side of the patch portion. The ACL contact pad 275 on the chin portion 271 is in physical and electrical contact with the ACL connector contact pad 235 such that impedance-based localization signals from the patient's body are transmitted via the transmitted through the ACL wires 280 extending through the single cable 264 exiting the sensor connector assembly 214. Magnetic based localization signals from the biosensor 290 are transmitted through the biosensor wires 292 also extending through the single cable exiting the sensor connector assembly.

It is understood that the ACL connector contact patch 235 (and thus, correspondingly the ACL contact pad 275 and the conducting trace 237), are not limited to the location illustrated herein. An advantage of the flex circuit member 221 is allowing the ACL connector contact patch 235 to be positioned in a variety of different locations as needed or appropriate so long as the patch 235 is supported by the structure of the connector portion 212 so that sufficient contact can be made when the sensor connector assembly is releasably engaged with the connector portion.

For either of the foregoing embodiments, it is advantageous to have the biosensor, ACL sensors and the sensor cable in the reusable sensor cable assembly in order to reduce the cost of the disposable patch assembly. The sensor cable assembly is connected to the patch assembly using an easy to operate insertion connection that is releasably held by the stops.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A patch and sensor assembly for use in a device mapping system for mapping location of a device within a body of a patient, comprising a reusable portion and a disposable portion, the reusable portion comprising:
a magnetic-based biosensor for providing location information of the device within the body to the device mapping system;
a housing adapted to house the biosensor, having a top portion and a bottom portion;
a first electrical lead for communicating an electrical signal from the biosensor to the device mapping system;
a first side member having a lesser thickness than the housing and extending laterally from a first side of the housing, the first side member having a first length that is shorter than a length of the housing; and
a second side member having a lesser thickness than the housing and extending laterally from a second side of the housing, the second side member having a second length that is shorter than the length of the housing;

the disposable portion comprising:
an adhesive hydrogel layer for adhering the disposable portion to the body of the patient;
an electrode layer disposed on the adhesive hydrogel layer;
a sensor engagement element adapted to detachably receive at least the first and second side members of the reusable portion,
wherein, the reusable portion includes a second electrical lead adapted to receive an electrical signal from the electrode layer when the reusable portion is releasably engaged with the sensor engagement element.

2. The patch and sensor assembly of claim 1, wherein the disposable portion further comprises at least one electrode member adapted to electrically couple the electrode layer and the second electrical lead when the reusable portion is releasably engaged with the sensor engagement element.

3. The patch and sensor assembly of claim 2, wherein the at least one electrode member is elastically movable relative to the sensor engagement element when in contact with the reusable portion.

4. The patch and sensor assembly of claim 1, wherein the reusable portion further includes a sensor adapted to transmit an electrical signal to the second electrical lead in response to the electrode layer.

5. The patch and sensor assembly of claim 1, wherein the sensor engagement element includes slots adapted to receive the first and second side members of the reusable portion.

6. The patch and sensor assembly of claim 1, wherein the disposable portion includes a flexible circuit member.

7. The patch and sensor assembly of claim 6, wherein the reusable portion includes an ACL contact member electrically coupled to the second electrical lead.

8. The patch and sensor assembly of claim 7, wherein the flexible circuit member includes first and second electrical conductors, the first conductor being responsive to the electrode layer and the second conductor being in electrical communication with the ACL contact member when the reusable portion is releasably engaged with the sensor engagement element.

9. The patch and sensor assembly of claim 7, wherein the flexible circuit member comprises:
a first segment disposed on the electrode layer of the disposable portion and comprising an electrode layer contact pad;
a second segment disposed on the sensor engagement element of the disposable portion and comprising an ACL connector contact pad;
and a conductor element extending between the electrode layer contact pad and the ACL connector contact pad, the conductor element configured to electrically connect the electrode layer contact pad and the ACL connector contact pad.

10. The patch and sensor assembly of claim 9, wherein the ACL contact member of the reusable portion is configured to contact the ACL connector contact pad when the reusable portion is releasably engaged with the sensor engagement element.

11. The patch and sensor assembly of claim 1, wherein the reusable portion includes an ACL contact member electrically coupled to the second electrical lead.

12. The patch and sensor assembly of claim 11, wherein the ACL contact member is on a patient-facing surface of the reusable portion.

13. The patch and sensor assembly of claim 11, wherein the ACL contact member is on an away surface of the reusable portion.

14. The patch and sensor assembly of claim 1, wherein the disposable portion includes stops that releasably engage proximal ends of the first and second side members of the reusable portion when the reusable portion is releasably engaged with the sensor engagement element.

15. The patch and sensor assembly of claim 1, wherein the electrode layer comprises carbon composite with at least one coating of a metallic material.

16. The patch and sensor assembly of claim 15, wherein the metallic material comprises silver chloride.

17. The patch and sensor assembly of claim 16, wherein the metallic material further comprises a layer of silver disposed on the silver chloride.

18. A patch and sensor assembly for use in a device mapping system for mapping location of a device within a body of a patient, comprising a reusable portion and a disposable portion, the disposable portion comprising:
an adhesive layer for adhering the disposable portion to the body of the patient;
an electrode layer disposed on the adhesive layer;
a sensor engagement element adapted to detachably receive at least a portion of the reusable portion; and
a flexible circuit substrate comprising a first portion disposed on at least a portion of the electrode layer and a second portion disposed on at least a portion of the sensor engagement element, the flexible circuit substrate comprising an active current location (ACL) connector contact pad;

the reusable portion comprising:
a magnetic-based biosensor for providing location information of the device within the body to the device mapping system;
a housing adapted to house the biosensor, having a top portion and a bottom portion;
a first electrical lead for communicating an electrical signal from the biosensor to the device mapping system;

a second electrical lead adapted to receive an electrical signal from the electrode layer when the reusable portion is releasably engaged with the sensor engagement element; and an ACL contact member, the ACL contact member configured to contact the ACL connector contact pad of the disposable portion when the reusable portion is releasably engaged with the sensor engagement element.

19. The patch and sensor assembly of claim 18, wherein the ACL connector contact pad is on the second portion of the flexible circuit substrate.

20. A patch and sensor assembly for use in a device mapping system for mapping location of a device within a body of a patient, comprising a reusable portion and a disposable portion, the disposable portion comprising:
an adhesive layer for adhering the disposable portion to the body of the patient;
an electrode layer disposed on the adhesive layer;
a sensor engagement element adapted to detachably receive at least a portion of the reusable portion; and
a flexible circuit substrate comprising:
a first segment disposed on the electrode layer of the disposable portion and comprising an electrode layer contact pad,
a second segment disposed on the sensor engagement element of the disposable portion and comprising the ACL connector contact pad, and
a conductor element extending between the electrode layer contact pad and the ACL connector contact pad, the conductor element configured to electrically connect the electrode layer contact pad and the ACL connector contact pad;

the reusable portion comprising:
a magnetic-based biosensor for providing location information of the device within the body to the device mapping system;
a housing adapted to house the biosensor, having a top portion and a bottom portion;
a first electrical lead for communicating an electrical signal from the biosensor to the device mapping system;
a second electrical lead adapted to receive an electrical signal from the electrode layer when the reusable portion is releasably engaged with the sensor engagement element; and
an ACL contact member, the ACL contact member configured to contact the ACL connector contact pad of the disposable portion when the reusable portion is releasably engaged with the sensor engagement element.

* * * * *